United States Patent [19]

Angsupanich

[11] Patent Number: 5,197,949
[45] Date of Patent: Mar. 30, 1993

[54] SUCTION IRRIGATION DEVICE WITH A SCRAPER

[76] Inventor: Kraivit Angsupanich, 801 11th St., Lakeport, Calif. 95453

[21] Appl. No.: 643,739

[22] Filed: Jan. 22, 1991

[51] Int. Cl.$^5$ ............................................. A61M 3/00
[52] U.S. Cl. ........................................ 604/35; 604/902; 128/758; 606/190
[58] Field of Search .................. 604/35, 43, 119, 266, 604/268, 269, 902, 22, 257, 261, 262; 128/657, 658, 17, 20; 606/190, 160; 433/91, 95, 157

[56] References Cited

U.S. PATENT DOCUMENTS

| | | | |
|---|---|---|---|
| 2,715,899 | 8/1955 | MacLean | 128/758 |
| 2,804,075 | 8/1957 | Borden | 604/902 |
| 3,335,727 | 8/1967 | Spoto | 604/119 |
| 3,495,593 | 2/1970 | Snyder | 606/190 |
| 3,964,484 | 6/1976 | Reynolds et al. | 604/902 |
| 4,043,322 | 8/1977 | Robinson | 128/758 |
| 4,049,000 | 9/1977 | Williams | 604/119 |
| 4,445,517 | 5/1984 | Feild | 604/35 |
| 4,708,717 | 11/1987 | Deane et al. | 604/266 |
| 4,715,848 | 12/1987 | Beroza | 604/902 |

Primary Examiner—John D. Yasko
Assistant Examiner—Anthony Gutowski
Attorney, Agent, or Firm—Malcolm B. Wittenberg

[57] ABSTRACT

A device for irrigation and suction removal of blood, bodily fluids and debris during surgery. A hollow tube is provided which contains an interior bore such that a vacuum force may be applied therethrough. The hollow tube also contains a secondary channel such as to allow sufficient quantities of water to dislodge any debris that may clog the interior bore during use in surgical procedures. A pivoting scraper is provided for facilitating the traction of an opening or wound.

1 Claim, 5 Drawing Sheets

5,197,949

SUCTION IRRIGATION DEVICE WITH A SCRAPER

TECHNICAL FIELD OF THE INVENTION

This invention relates generally to a device for the irrigation and suction removal of bodily fluids and debris primarily during surgery. The device has the capability of providing a suction force to remove blood, bodily fluids and debris and of providing a source of water to prevent and dislodge any debris which may otherwise clog the device or connecting tube. A scraper means may also be provided to facilitate traction of an incision or wound.

BACKGROUND OF THE INVENTION

It is a common medical practice during surgery to provide a suction force to a surgical incision so as to remove blood, bodily fluids and debris primarily during surgery. The procedure is generally accomplished by the use of a plastic tubular device attached to a suction source. The end of the device is placed near or at a surgical incision so as to remove the bodily fluids and debris from the area.

In the use of the above-described device a problem develops during surgery in that the end of the tube becomes clogged with debris. Thus, valuable time and effort must be expended by the practitioner in order to clear the device of any debris clogged in the device.

Further, incisions tend to close during surgery so that personnel involved in the surgery must also expend valuable time and effort during the surgery to facilitate traction of the incision or wound.

It is thus an object of the present invention to provide a convenient device which enables the practitioner to apply a suction force to a surgical site while also providing an irrigation stream which acts to irrigate the wound and to dislodge any clogging debris in the device or suction tube.

It is yet a further object of this invention to provide the practitioner with an attachment to the device which allows the practitioner to have a convenient means for facilitating traction of an incision or wound.

It is still yet a further object of this invention to provide the practitioner with a convenient light-weight hand-held device so as to allow the practitioner to provide a suction force, irrigation stream and scrapper means by use of the device quickly and efficiently during surgery without the loss of valuable time and effort.

These, and further objects of the present invention, will be further appreciated when considering the following disclosure and appended drawings, wherein.

SUMMARY OF THE INVENTION

The present invention deals with a device for the irrigation and suction removal of bodily fluids and debris primarily during surgical procedures. The device comprises an elongated substantially hollow tube sized to be comfortably held by the human hand. The tube has an upstream end configured to be attached to a suction hose and a downstream end. The upstream and down stream ends are connected by a longitudinally extending interior bore.

A secondary channel is contained within the substantially hollow tube and is characterized as having an upstream end configured to attach a source of water and a downstream end configured to discharge the water within the longitudinally extending interior bore proximate to its downstream end. A scraper means located proximate the downstream end of the hollow tube may be provided for facilitating traction of an opening or wound.

DETAILED DESCRIPTION OF THE INVENTION

Figure 1:
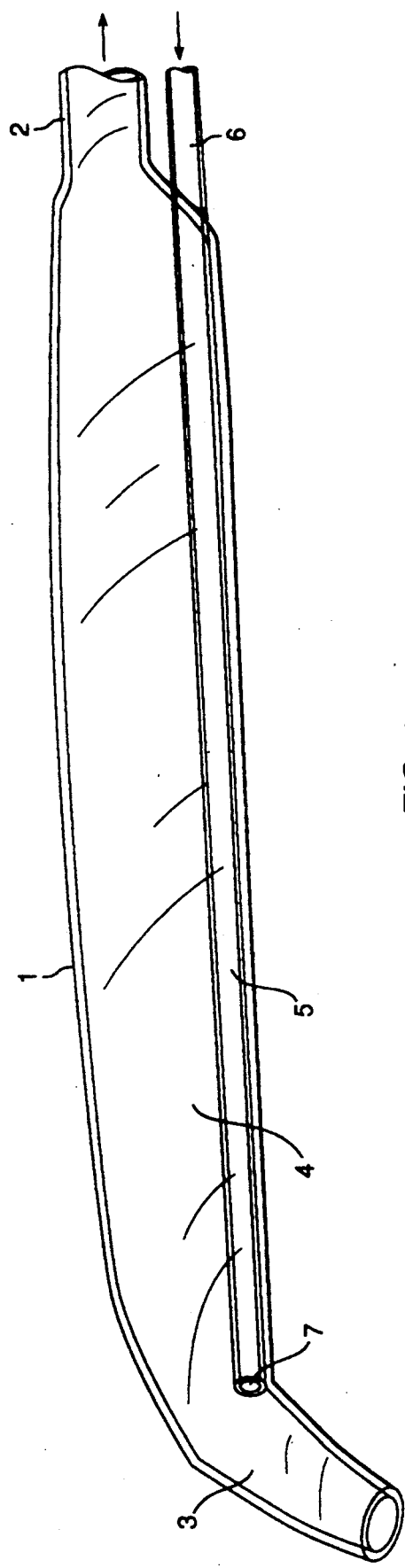
FIGS. 1 to 3 and 6 are side plan views of the device of the present invention.

The present invention can be more readily appreciated when considering FIGS. 1 to 9. In FIG. 1 an elongated substantially hollow tube 1 is shown with an upstream end 2 and a downstream end 3. The upstream end 2 is configured to be attached to a vacuum hose. The upstream and downstream ends are connected by a longitudinally extending interior bore 4.

A secondary channel 5 contained within the substantially hollow tube 1 is shown in FIG. 1 having an upstream end 6 configured to attach to a source of water and a downstream end 7 configured to discharge the water within the longitudinally extending interior bore 4 proximate its downstream end 3.

Figure 2:
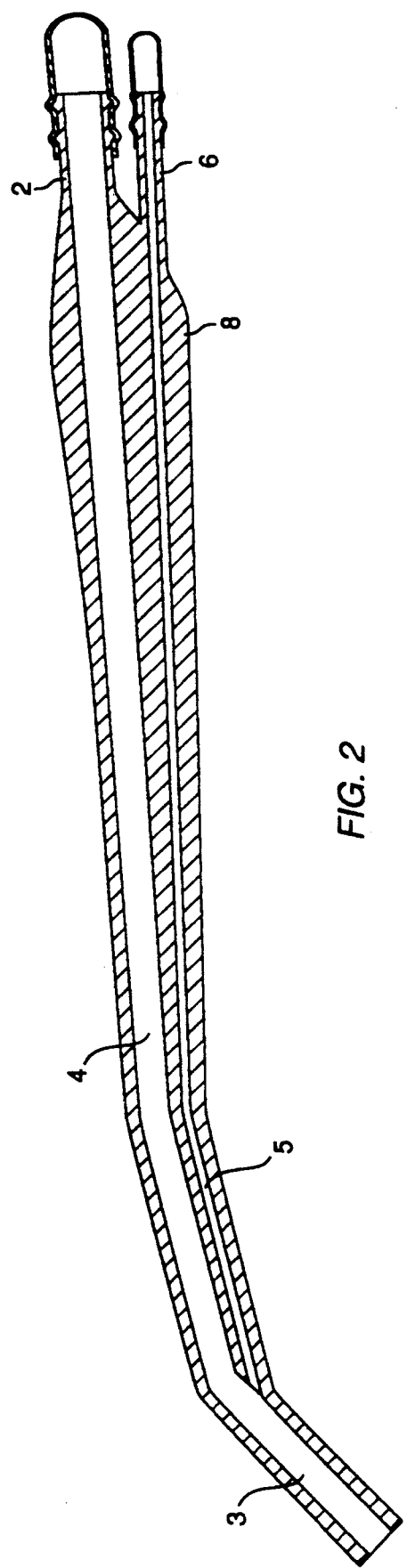

An embodiment of the present invention can be appreciated when examining FIG. 2 where the longitudinally extending bore 4 is sized so as to suctionally remove blood, bodily fluids and debris normally found during surgical procedures.

FIG. 2 also displays an example of an embodiment of the present invention with a secondary channel 5 contained within the substantially hollow tube and extending longitudinally through a thickened bottom wall 8 of the hollow tube 1. Secondary channel 5 is sized to discharge water proximate the downstream end 3 of the interior bore 4 in sufficient quantities so as to dislodge expected debris that may otherwise clog the interior bore or the connecting tube during use in surgical procedures.

Figure 3:
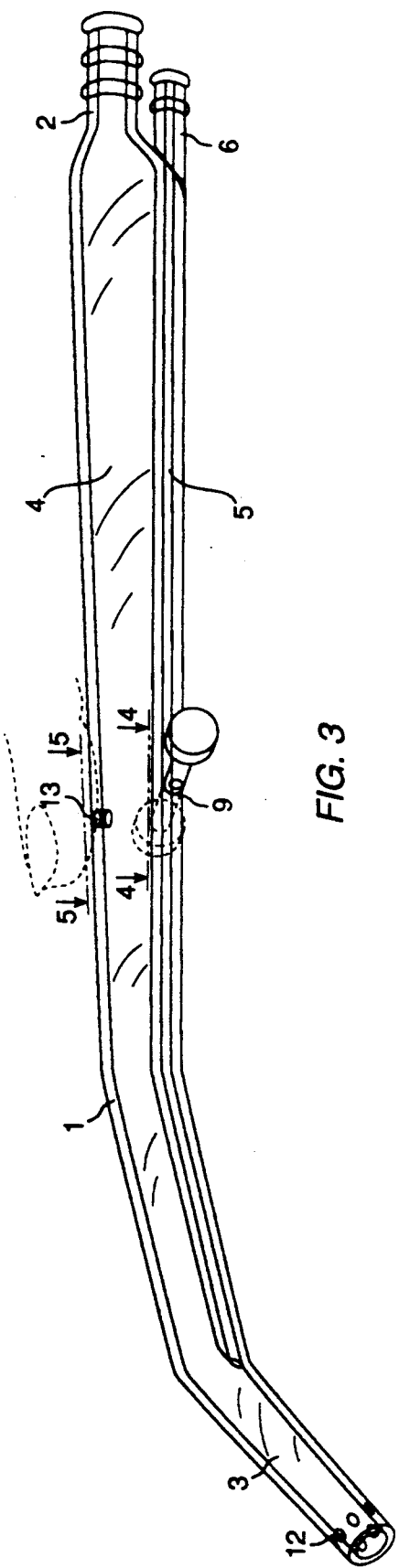
Figure 4A:
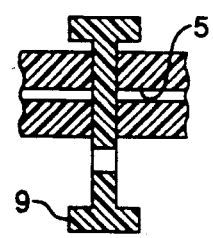
FIG. 4 illustrates valve arrangements for controlling water flow in the present invention.
Figure 4B:
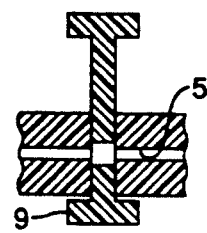

Another example of an embodiment of the present invention is illustrated in FIG. 3. The secondary channel 5 is configured with a valve means 9 so that the practitioner may control the flow of water within the secondary channel 5 as needed. Thus FIG. 4 displays the valve means 9 having an open position 10 and a closed position 11 so as to enable the practitioner to shut-off and turn-on the stream of water through the secondary channel 5.

FIG. 3 further displays the invention possessing a plurality of openings 12 radially extending through the side wall of the hollow tube 1 proximate its downstream end to facilitate the vacuum removal of surgical debris or fluid.

Figure 5:
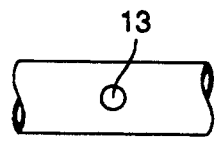
FIG. 5 is an enlarged segment of the device of the present invention depicting the preferred embodiment of providing a hole in the side wall of the device to control vacuum therein.
Figure 7:
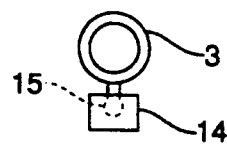
FIGS. 7 and 8 illustrate the scraper element of the present invention.
Figure 8:
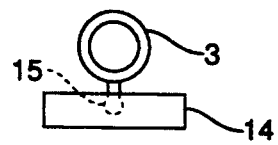
Figure 9:
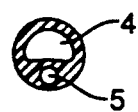
FIG. 9 is a cross-sectional view of the present invention taken along line 9—9 of FIG. 6.

The invention embodied in FIG. 3 is further characterized as possessing an opening 13, FIG. 5, in the side wall of the hollow tube 1 positioned such that a user of the device can conveniently use a finger to block or free the opening 13 in order to control the vacuum pressure being drawn at the downstream end 3.

Figure 6:
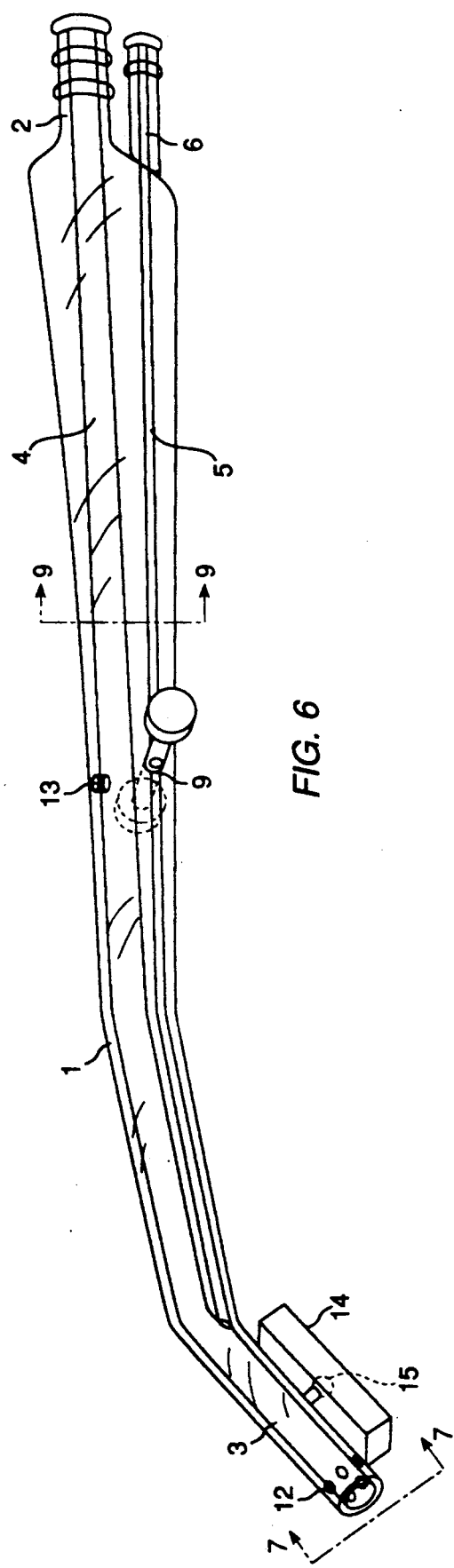

A preferred embodiment can be appreciated when considering FIG. 6. The invention as displayed in FIG. 6 is a convenient hand-held device constructed of a preferably transparent plastic material such as polypropylene or polyethylene. During surgery it is useful for the practitioner to be able to remove blood, bodily fluids and debris from a surgical site and to also be able to maintain and facilitate the opening of a surgical incision. The ability of a practitioner to carry out these functions are enhanced when the practitioner is provided with a device which is embodied in a plastic, light-weight device wherein all the functions can be carried out quickly and efficiently by hand during surgery. Thus, the invention as described in the preferred embodiment allows a practitioner to hold the device in hand while applying a vacuum to a surgical site. The practitioner may also place a human finger over the suction whole 13 which allows the maintenance of a vacuum pressure throughout the interior bore 4. Alternatively, the practitioner may remove the finger from the suction hole 13 to allow a stream of water to flow through the secondary channel 5 whenever it is necessary to dislodge debris clogged in the interior bore 4 or when the incision needs to be irrigated.

Further, the practitioner has the immediate availability of a substantially planar extension scrapper means 14 located proximate the downstream end of the hollow tube 1 for facilitating traction of an opening or wound. The scraper means 14 as illustrated in the present embodiment of the invention is capable of pivoting about a universal joint 15 so as to allow the scraper to be parallel (FIG. 7) and perpendicular (FIG. 8) to the longitudinally extending interior bore 4.

The preferred dimensions of the longitudinally extending interior bore 4 is approximately 1.0 cm in diameter so as to allow a sufficient suction force to remove blood, bodily fluids and debris found during surgical procedures. The preferred dimensions of the secondary channel is sized at approximately 0.3 cm in diameter. The preferred dimension of the opening 13 is approximately 0.3 cm in diameter so as to allow a human finger to block and free the opening in order to control the vacuum pressure being drawn at the downstream end 3 of the longitudinally extending interior bore 4. To facilitate the vacuum removal of surgical debris a plurality of openings 12 are shown radially extending through the side wall of the hollow tube 1 where each opening preferably has a diameter of approximately 0.2 cm.

What is claimed is:

1. A device for the irrigation and suction removal of bodily fluids and debris primarily during surgical procedure comprising an elongated substantially hollow tube sized to be comfortably held by the human hand, said tube having an upstream end configured to be attached to a vacuum hose and a downstream end, said upstream and downstream ends being connected by a longitudinally extending interior bore and a secondary channel also contained within said substantially hollow tube characterized as having an upstream end attached to a source of water and a downstream end configured to discharge said source of water within said longitudinally extending interior bore proximate its downstream end and further comprising a scraper means located proximate the downstream end of said elongated substantially hollow tube for facilitating traction of an opening or wound, said scraper means comprising a substantially planar extension to said hollow tube pivotable so as to be capable of being both parallel to and perpendicular to said longitudinally extending interior bore.

* * * * *